(12) United States Patent
Wong et al.

(10) Patent No.: US 9,115,050 B2
(45) Date of Patent: Aug. 25, 2015

(54) PROCESS FOR IMPROVED RECOVERY OF ONIUM HYDROXIDE FROM COMPOSITIONS CONTAINING PROCESS RESIDUES

(71) Applicant: SACHEM, INC., Austin, TX (US)

(72) Inventors: Sharon Wong, Higashi Osaka (JP); Ryuichi Otogawa, Higashi Osaka (JP)

(73) Assignee: Sachem, Inc., Austin, TX (US)

( * ) Notice: Subject to any disclaimer, the term of this patent is extended or adjusted under 35 U.S.C. 154(b) by 135 days.

(21) Appl. No.: 14/143,908

(22) Filed: Dec. 30, 2013

(65) Prior Publication Data

US 2015/0183717 A1 Jul. 2, 2015

(51) Int. Cl.
*C07C 221/00* (2006.01)
*C07C 209/86* (2006.01)

(52) U.S. Cl.
CPC .................................. *C07C 209/86* (2013.01)

(58) Field of Classification Search
CPC .................................................. C07C 221/00
See application file for complete search history.

(56) References Cited

U.S. PATENT DOCUMENTS 5,439,564 A    8/1995    Shimizu et al.
6,508,940 B1    1/2003    Niinobe

OTHER PUBLICATIONS

European Search Report for corresponding European Application No. 14197283.6 dated Jun. 2, 2015.

*Primary Examiner* — Rosalynd Keys
*Assistant Examiner* — Jennifer C Sawyer
(74) *Attorney, Agent, or Firm* — Renner, Otto, Boisselle & Sklar, LLP (57) ABSTRACT

A process for recovering an onium hydroxide from a composition containing onium ions and a process residue, including providing a composition containing onium ions and a process residue; adding a quantity of a surfactant to the composition to obtain a surfactant-modified composition; providing a cation exchange media; collecting the onium ions by applying the surfactant-modified composition to the cation exchange media wherein the onium ions become bound to and retained by the cation exchange media and the process residue and the surfactant do not become bound to the cation exchange media and are substantially not retained by the cation exchange media; and recovering the onium ions from the cation exchange media as an onium hydroxide by applying a cation-containing hydroxide composition to the cation exchange media.

21 Claims, 4 Drawing Sheets

PROCESS FOR IMPROVED RECOVERY OF ONIUM HYDROXIDE FROM COMPOSITIONS CONTAINING PROCESS RESIDUES

TECHNICAL FIELD

The present invention relates to recovery of onium hydroxides from process residues such as tetramethylammonium hydroxide from photoresist-containing process residues.

BACKGROUND

Onium hydroxides, such as tetramethylammonium hydroxide, are used in processing of semiconductors and in processing of flat panel display devices, e.g., liquid crystal display (LCD) devices. Environmental and economic concerns drive the desire to recycle materials, including materials such as the onium hydroxides used in processing of semiconductor and flat panel devices. Materials such as onium hydroxides and onium salts are the subject of rather stringent environmental regulations. The production of new onium hydroxides and onium salts is more expensive than is the recycling of used onium hydroxides and onium salts. Use of materials such as onium hydroxides in semiconductor and liquid crystal display processing inevitably contaminates the onium hydroxides with process residues such as photoresist residues. While removal of most process residues and recovery of the onium hydroxides from waste mixtures from such processing has been known, it has proven quite difficult efficiently to remove process residues such as photoresist residues and similar materials from such waste mixtures without creating problems in the recycling process. In ion exchange processes for recycling onium ions, problems include channeling, early breakthrough and resulting loss of ion exchange capacity, as a result of the presence of the process residues. In order to meet this need and overcome these problems, it has been generally necessary to conduct such recovery operations at a level of efficiency that is lower than that theoretically possible based on the loading of onium hydroxides in the waste mixtures and the known ion exchange capacity of the ion exchange resins used for such recovery, since heretofore it has been impossible to attain removal of such contaminants from recycled onium hydroxide-containing waste mixtures at higher efficiencies. Thus, it has proven difficult to recycle materials such as the onium hydroxides used in processing of semiconductor and flat panel display devices for re-use in subsequent processing of semiconductor and flat panel display devices. Removal of residues such as photoresist residues from recycled onium hydroxide and salt solutions has been a long-standing problem, and a need remains for such methods, if materials such as onium hydroxides and salts are to be successfully and economically recycled for use in the most demanding applications, such as in semiconductor and flat panel display processing.

SUMMARY

The present invention provides a solution to the problem of recycling onium hydroxide solutions while efficiently removing process residues such as photoresist residues to recover onium hydroxides acceptable for re-use of the recovered onium hydroxide or salt solutions in the most demanding applications.

The present invention provides a recovery process in which a selected surfactant is added to a residue-containing waste solution containing an onium compound, and using a cation exchange resin. The waste solutions also contain residues of etched photoresists which are used extensively in semiconductor and TFT-LCD flat panel fabrications. The surfactant is a nonionic, water soluble polymer comprising repeating units of carbon monomers and hydroxyl substituents, having a molecular weight typically between about 1000 and about 2,000,000. As the waste material passes through the cation exchange resin and the onium ions therein are taken up by the cation exchange resin, the pH of the waste solution decreases substantially, from a pH in the range of about 13-14 down to a pH in the range from about pH 3 to about pH 4. Photoresist residues generally are insoluble at low pH, and if no action is taken, will precipitate in or onto the cation exchange media resulting in poor flow distribution and inefficient utilization of the cation exchange capacity of the media. In accordance with the present invention, addition of the selected surfactant enhances solubility of the photoresist residues when the surfactant molecule wraps itself around the photoresist polymer chains. As a result, the photoresists remain soluble and can be removed smoothly from the column without significant pressure build-up or flow restriction.

In accordance with one embodiment of the present invention, there is provided a process for recovering an onium hydroxide from a composition containing onium ions and a process residue, including:

providing a composition containing onium ions and a process residue;

adding a quantity of a surfactant to the composition to obtain a surfactant-modified composition;

providing a cation exchange media;

collecting the onium ions by applying the surfactant-modified composition to the cation exchange media wherein the onium ions become bound to and retained by the cation exchange media and the process residue and the surfactant do not become bound to the cation exchange media and are substantially not retained by the cation exchange media; and recovering the onium ions from the cation exchange media as an onium hydroxide by applying a cation-containing hydroxide composition to the cation exchange media.

In one embodiment, the process further comprises loading the cation exchange media into at least one vessel. In one embodiment, the process further comprises loading the cation exchange media into at least two vessels connected in a series, in which a first effluent from a first vessel of the at least two vessels may be applied as feed to a second vessel of the at least two vessels. In some embodiments, the vessel is a column.

In one embodiment, in the collecting, the surfactant-modified composition is applied to the cation exchange media in the first vessel, the first effluent is applied as the feed to the second vessel, and the recovering is carried out on at least the first vessel when a predetermined pH change is detected in a second effluent from the second vessel.

In one embodiment, in the collecting, the surfactant-modified composition is applied to the cation exchange media in the first vessel, the first effluent is applied as feed to the cation exchange media in the second vessel, and a second effluent from the second vessel is applied as feed to the cation exchange media in a third vessel of the at least two vessels and a third effluent is obtained.

In one embodiment, the collecting is continued until a predetermined pH change is detected in the third effluent from the third vessel.

In one embodiment, the recovering is carried out following detection of the predetermined pH change.

In one embodiment, following the detection of the predetermined pH change, the third effluent is fed to a fourth vessel, and the collecting continues.

In one embodiment, the process residue comprises a photoresist residue.

In one embodiment, the onium is a quaternary ammonium. In one embodiment, the quaternary ammonium has a general formula (I):

(I)

wherein in formula (I), $R^1$, $R^2$, $R^3$ and $R^4$ are each independently an alkyl group containing from 1 to about 8 carbon atoms. In one embodiment, each R is methyl, and in another embodiment each R is butyl.

In one embodiment, the surfactant is a hydroxyl-containing nonionic surfactant. In one embodiment, the surfactant is a hydroxyalkylcellulose, wherein the alkyl is methyl, ethyl, propyl or butyl. In one embodiment, the surfactant is a hydroxyethylcellulose. In one embodiment, the hydroxyethylcellulose has a molecular weight in the range from about 10,000 to about 1,000,000, or from about 100,000 to about 500,000, preferably about 250,000.

In one embodiment, the hydroxyl-containing nonionic surfactant is a poly(ethyleneglycol) having a molecular weight in the range from about 20,000 to about 2,000,000, preferably about 200,000.

In one embodiment, the surfactant is a poly(vinylalcohol) (PVA) having a molecular weight in the range from about 20,000 to about 2,000,000, preferably about 66,000 to about 80,000.

In one embodiment, the surfactant is a guar gum.

In one embodiment, the quantity of the selected surfactant in the surfactant-modified composition is in the range from about 10 ppm to about 10,000 ppm based on the total quantity of the surfactant-modified composition.

In one embodiment, the cation-containing hydroxide is sodium hydroxide, potassium hydroxide, lithium hydroxide, or a combination of any two or more thereof.

In one embodiment, the process further includes regenerating the cation exchange media by applying an acid to the cation exchange media.

In accordance with embodiments of the processes of the present invention, residues such as photoresist residues can be removed and recycled onium hydroxide and/or salt solutions can be recovered for further purification and eventual re-use in processing of semiconductor and flat panel display devices.

Thus, the present invention addresses the problem of recycling onium hydroxide and salt containing compositions to provide recycled high purity onium hydroxide solutions. The recycled high purity onium hydroxides obtained by the process of the present invention contain very low levels of processing residues such as photoresist residues, and are acceptable for use of the recycled materials in demanding uses, such as in processing of semiconductor and flat panel display devices.

It should be appreciated that the process steps and structures described herein may not provide a complete system or process flow for carrying out a recycling process for onium hydroxide and/or salt solutions, such as would be used in a recycling facility for such materials. The present invention may be practiced in conjunction with techniques and apparatus currently used in the art, and only so much of the commonly practiced materials, apparatus and process steps are included as are necessary for an understanding of the present invention.

DETAILED DESCRIPTION

As set forth above, the present invention relates to a process for recovering an onium hydroxide from a composition containing onium ions and a process residue. The onium hydroxide and/or onium salt solutions applied to the present process may be recovered from, e.g., semiconductor or liquid crystal display processing and from other processes which include the use of onium hydroxide and/or salt solutions. In one embodiment, the present invention is applicable to onium hydroxide solutions. In one embodiment, the present invention is applicable to onium salt solutions. In one embodiment, the onium hydroxides obtained with the present invention may be further purified by processes known to those of skill in the art. Such conversion processes include those disclosed in the present applicant's U.S. Pat. No. 6,508,940, as well as in commonly assigned U.S. Pat. Nos. 6,787,021; 6,217,743; 6,207,039; 5,968,338; 5,951,845; 5,910,237; 5,868,916; 5,853,555; and 5,833,832, the disclosure of each of which is incorporated herein by reference for the teachings relating to conversion of onium salts into onium hydroxides and to purification of the onium hydroxides by various methods. While those processes and disclosures relate to conversion and purification of onium hydroxides, the present invention primarily relates to recycling such onium hydroxide and/or onium salt solutions, and in particular to removing residues such as photoresist residues from the recycled onium hydroxide and/or onium salt solutions for re-use of the recycled onium hydroxide and/or onium salt solutions in the most demanding industries, such as the semiconductor and flat panel display device industries. In one embodiment, the present invention is applicable to compositions containing primarily onium hydroxides and, in some cases, some amount of the corresponding salts. Thus the reference herein to onium ions includes both the to onium hydroxide and the salt.

Thus, in one embodiment, the present invention provides a process for recovering an onium hydroxide from a composition containing onium ions and a process residue, including:

providing a composition containing onium ions and a process residue; adding a quantity of a surfactant to the composition to obtain a surfactant-modified composition;

providing a cation exchange media;

collecting the onium ions by applying the surfactant-modified composition to the cation exchange media wherein the onium ions become bound to and retained by the cation exchange media and the process residue and the surfactant do not become bound to the cation exchange media and are substantially not retained by the cation exchange media; and recovering the onium ions from the cation exchange media as an onium hydroxide by applying a cation-containing hydroxide composition to the cation exchange media.

As used herein, "collection", when applied to onium ions, refers to the capture of onium ions by a cation exchange medium. Thus, the onium ions are "collected" from the composition comprising onium ions and a process residue.

As used herein, "recovery", when applied to onium ions, refers to the removal of the collected onium ions from the cation exchange media, by application, e.g., of a strong base, such as sodium hydroxide, to the media. Thus, the onium ions are "recovered" from the cation exchange media.

The following detailed description provides additional details relating to this process. Further details are known to or can be readily developed by those of skill in the art, based on the following descriptions and examples.

Organic Onium Hydroxides and Onium Salts

In one embodiment, the composition containing onium ions and a process residue may comprise an organic onium hydroxide and/or organic onium salt. Suitable organic onium hydroxides and salts for the present invention include organic onium hydroxides such as quaternary ammonium hydroxides, quaternary phosphonium hydroxides, tertiary sulfonium hydroxides, tertiary sulfoxonium hydroxides and imidazolium hydroxides, and the corresponding salts. Herein, any reference to "onium hydroxide and/or salt" refers to either or both of organic onium hydroxide and/or organic onium salt, unless clearly, specifically limited to one or the other.

In the following description of exemplary onium ions, the specific embodiments shown below are the hydroxides. It is to be understood that in the following disclosure, unless specifically limited to onium hydroxides, the corresponding onium salts are included, since both the hydroxide and the salt(s) may be present in the composition containing onium ions and a process residue. Those of ordinary skill in the art will understand that the onium salt may be determined based on the disclosure relating to the onium hydroxides, with appropriate adjustments for the charge on the anion forming the onium salt. That is, where the salt is formed from a singly charged onium ion (cation) and a singly charged anion, such as a halide, there will be a single onium ion for each anion, and where the salt is formed from a singly charged onium ion and a doubly charged anion, such as a sulfate, $SO_4^=$, there will be two onium ions for each doubly charged anion.

Possible anions in the onium salts include anions of common acids. Such anions include, for example, a halide ion, a sulfate, hydrogen sulfate or alkylsulfate anion, a carboxylate anion, a nitrate anion, a carbonate, bicarbonate or alkyl carbonate anion, a phosphate, hydrogen phosphate or dihydrogen phosphate anion, a sulfonate anion, an alkylsulfonate anion, etc. Thus, in one embodiment, in the following formula (I), the OH group can be replaced with an "X" group, where the X represents the anion, and "x" may be an integral value or a non-integral value, such as ½ or ⅓. In another embodiment, the number of onium moieties A can be selected to balance an integral number of "X" groups as needed to obtain a balanced, neutral salt.

In one embodiment, the onium hydroxides may generally be characterized by the formula I:

$$A(OH)_x \tag{I}$$

wherein A is an onium group and x is an integer equal to the valence of A. Examples of onium groups include ammonium groups, phosphonium groups, sulfonium, sulfoxonium and imidazolium groups. As noted above, a suitable anion may be substituted for the hydroxide, to form the corresponding onium salt.

In one embodiment, the onium is a quaternary ammonium. In one embodiment, the quaternary ammonium ion has a general formula (II):

wherein in formula (I), $R^1$, $R^2$, $R^3$ and $R^4$ are each independently an unbranched or branched alkyl group containing from 1 to about 8 carbon atoms. In one embodiment, each or $R^1$, $R^2$, $R^3$ and $R^4$ is methyl, and in another embodiment, each $R^1$, $R^2$, $R^3$ and $R^4$ is butyl. In embodiments in which the other mentioned onium ions are present, the R groups on each such onium moiety may be selected from the same group of $R^1$, $R^2$, $R^3$ and $R^4$, as appropriate to the number of R groups present on any given onium moiety. That is, for sulfonium and sulfoxonium, each of which contain three R groups, $R^1$, $R^2$ and $R^3$, and for imidazolium, which contains two R groups, $R^1$ and $R^2$, each such R group is as defined above for the quaternary ammonium moiety.

The concentration of the onium hydroxide and/or salt in the composition containing onium ions and a process residue of the present invention may range up to about 25 wt % of the recycled composition. In one embodiment, the onium hydroxide and/or salt concentration is in a range from about 1 wt % to about 20 wt %, and in another embodiment, the onium hydroxide and/or salt concentration is in a range from about 2 wt % to about 10 wt %, all concentrations based on the total weight of the recycled composition containing onium ions and a process residue. Higher concentrations may be diluted for use in the process of the present invention.

Ion Exchange Resin

In one embodiment, the process of the present invention is carried out using any suitable, known cation exchange resin, e.g., either of a strong acid cation exchange resin or a weak acid cation exchange resin. It is preferred to carry out the process of the present invention using a weak acid cation exchange resin, since the weak acid form functions satisfactorily and so it is not necessary to use a stronger acid resin. Experiments suggest that strong acid ion exchange resins, such as sulfonic acid resins, may be less or not useful in the present invention. However, it may be possible to use a strong acid ion exchange resin under the appropriate conditions, as known in the art.

Suitable weak acid ion exchange resins are commercially available. The present invention is not limited to any particular weak acid ion exchange resin. In general, weak acid ion exchange resins are carboxylate-type resins, in which the "active" sites are carboxyl groups.

Commercially available weak acid ion exchange media include, for example, acrylic based weakly acidic cation exchange resins such as PUROLITE®, available from The Purolite Company; DIAION®, available from Mitsubishi Chemical Corp.; DOWEX® and AMBERLITE™, available from The Dow Chemical Co.; or LEWATIT®, available from Lanxess AG. Suitable specific weak acid resins can be selected by the skilled person. Examples of possibly suitable weak acid ion exchange media which may be used in accordance with the present invention are disclosed, for example, in U.S. Pat. Nos. 4,595,508, 5,665,783, and 6,508,940, and are not intended to be limiting to the scope of the invention. Each of the foregoing patents may be consulted for additional information on various weak acid ion exchange resins, and are incorporated herein by reference for their teachings relating to such resins. Suitable ion exchange media may be selected by those of ordinary skill in the art, and may vary, for example, based on the specific onium ions and specific process residues dealt with in the specific process generating the composition to be recycled.

Ion Exchange Vessel or Column

In one embodiment, the process of the present invention is carried out in any suitable, known vessel in which ion exchange processes are routinely carried out. In one embodiment, the vessel is or includes a column, in which the weak acid ion exchange medium is loaded into a suitably sized and shaped column. The size and shape of the vessel or column may be suitably selected by the skilled person, based on the volume of the composition to be treated, the concentrations of both onium ions and process residue in the composition, and other factors known in the art of chromatographic separations. In one embodiment, the process is carried out in at least two columns connected in a series relationship, and in one embodiment in at least three columns connected in series. In one embodiment, each column is vertically oriented to allow for passage of at least some liquid materials through the column by gravity. As will be understood by those of ordinary skill in the art, a pump may also be used in either a downwardly or upwardly flowing column, for example, to increase the flow rate that would be obtained by gravity alone, or for other reasons. As also will be understood, if the column is vertically oriented, to obtain countercurrent flow, i.e., to have the liquid flow upward through the column, a pump or other means may be used. Such other means may include, for example, a reservoir of liquid material held at a position above the column, so that gravity can be used as the driving force for the countercurrent flow of the liquid material up through the column. Any suitable liquid transfer means known in the art may be used.

In one embodiment, the column is formed of a relatively inert or chemically unreactive material. Thus in one embodiment, the column may be fabricated of a glass or in another embodiment of a fluorinated polymer. Fluorinated polymers have excellent resistance to various solvents and chemicals, including organic solvents and strong bases, and may be used. Examples include polyethylene, polypropylene, Teflon®, AVATREL®, a functionalized polynorbornene from BFGoodrich, polyvinylidene fluoride (PVDF), Dyneon™ THV Fluorothermoplastic (a fluorinated terpolymer from 3M, St. Paul Minn.), HOSTAFLON™ TF 5035 (a PTFE modified with a perfluoroalkylether from 3M), fluorinated ethylene propylene (FEP), polytetrafluoroethylene (PTFE), and perfluoroalkoxy polymer (PFA), among others. Any suitable material may be selected for use as the column.

As will be recognized, it is not necessary for the vessel or column to be oriented in any particular direction or orientation. The vessel may be vertical, horizontal, coiled or arranged in any suitable way, provided that it can be loaded with the ion exchange medium and that the appropriate liquids can be passed through the vessel in a manner in which all of the liquids can come into contact with the ion exchange media.

Figure 1A:
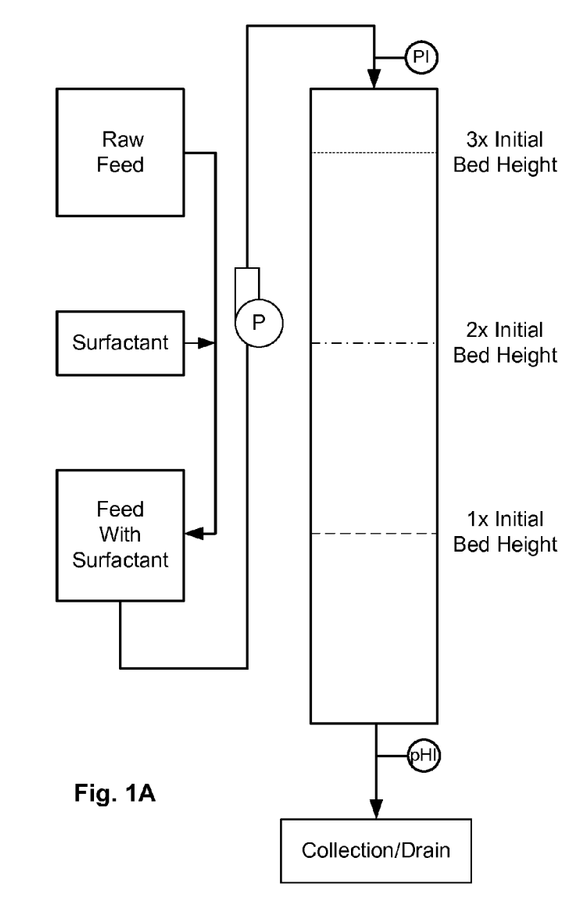
FIGS. 1A, 1B and 1C are a schematic depictions of three embodiments of a system for use in a process for recovering an onium hydroxide from a composition containing onium ions and a process residue in accordance with certain embodiments of the invention.
Figure 1B:
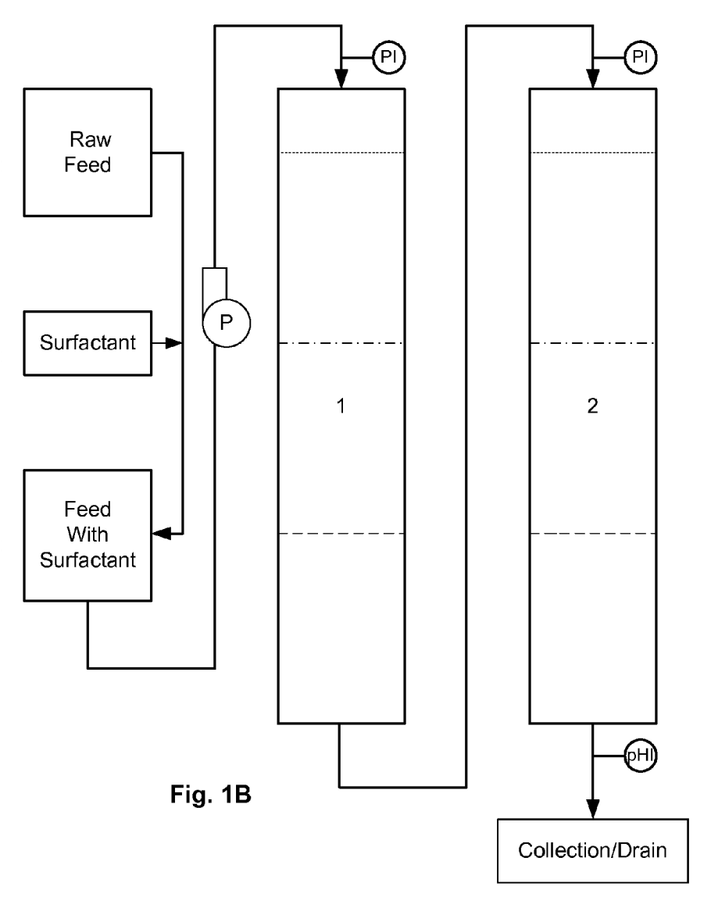
Figure 1C:
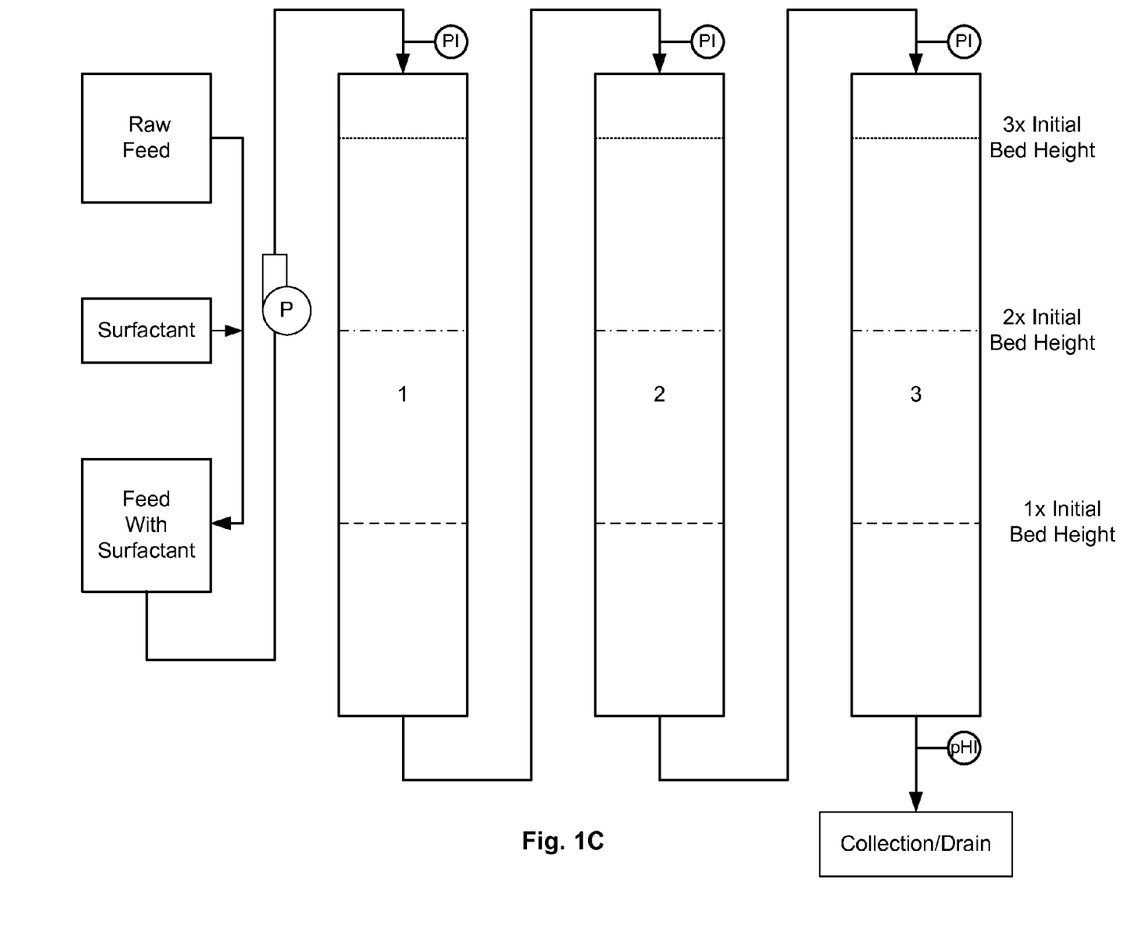

FIGS. 1A, 1B and 1C are a schematic depictions of three embodiments of a system for use in a process for recovering an onium hydroxide from a composition containing onium ions and a process residue in accordance with certain embodiments of the invention.

FIG. 1A depicts a single vessel embodiment of a system for use in the present invention. As shown in FIG. 1A, a raw feed, containing a composition containing onium ions and a process residue is provided. To this raw feed, a surfactant is added and the combined raw feed with the surfactant is pumped by a pump P into the vessel. As shown in FIG. 1A, the vessel is provided with and contains a bed of cation exchange media, and initially, it has an initial bed height, shown as "1× Initial Bed Height". The pressure of the feed to the vessel is monitored by a pressure indicator PI. As the combined raw feed with the surfactant is pumped into the vessel, the onium ions are absorbed by the cation exchange media, and the surfactant and any photoresist or other residue in the feed remains soluble or dispersed and passes through the vessel, and is collected and sent for disposal as appropriate. Thus, the surfactant-modified composition is applied to the cation exchange media during which the onium ions become bound to and retained by the cation exchange media and the process residue and the surfactant do not become bound to the cation exchange media and are substantially not retained by the cation exchange media, in accordance with the present invention.

As noted, the pressure of the feed is monitored by the pressure indicator, PI, to provide an additional indication of possible blockage of the column by precipitated process residues. If precipitation occurs, the backpressure will increase in the vessel or column, and this can be observed at the pressure indicator.

Referring still to FIG. 1A, as the collection step of the inventive process continues, the bed of cation exchange media swells due to the absorption of the onium ions, and may swell to twice or greater the original volume, as depicted by the "2× Initial Bed Height" and "3× Initial Bed Height". In general, during the collecting step of the process of the present invention, the cation exchange resin will swell to greater than 2×, but less than 3×, its initial bed height. If the total swelling is too small, it may indicate that the photoresist or other residue has partially blocked the vessel and resulted in channeling of the flow, and incomplete utilization of the cation exchange media's onium ion-absorption capacity. It is preferred that the bed height should increase to at least 2.3× the initial bed height. As is known in the art, the swelling of the cation exchange media results from replacement of the hydrogen ions, $H^+$, ionically bonded to the anionic sites of the cation exchange media, by the much larger onium ions, such as the tetramethylammonium ion, $TMA^+$, which replace the hydrogen ions and become ionically bonded to the anionic sites.

In one embodiment, the progress of the absorption of onium ions by the cation exchange media is monitored by monitoring the pH of the effluent from the vessel. As will be understood, as the onium ions are removed from the feed, the pH of the fluid in the vessel will decrease, for example, to a value in the range from about pH 3 to about pH 4. As long as the pH of the vessel effluent remains in the low range, it can be safely assumed that the onium ion capacity of the column has not been reached. When the observed pH of the vessel effluent begins to rise, e.g., to pH 6, this means that some onium ions may be escaping the column and the column may be considered to have reached its onium ion-absorption capacity. At this point, the feed to the vessel is stopped.

When the cation exchange media has adsorbed onium ions to its ion capacity, the vessel may be rinsed with additional water, or a solution of the same surfactant as a rinse, followed by a water rinse. The onium ions may be recovered from the cation exchange media as an onium hydroxide by applying a selected cation-containing hydroxide composition to the cation exchange media, and then the recovered onium hydroxide can be further purified if need be. The onium ions may be recovered as the corresponding onium hydroxide by applying a strong inorganic base such as sodium hydroxide, potassium hydroxide or lithium hydroxide, or a combination of any two or more thereof. In one embodiment, the strong base is a highly purified strong base containing very low levels of other metal ions and other impurities. Such highly purified, strong inorganic bases are commercially available. In general, sodium hydroxide is preferred due to cost and availability of high-purity material.

It is noted that the ion capacity of a cation exchange medium may vary if some portion of the medium is blocked by precipitated process residue. The present invention is directed to avoiding this problem by adding the surfactant to maintain the process residue in a solubilized condition, so that it will not precipitate and thereby block some of the cation exchange media and reducing the ion capacity of the media.

Thus, in the embodiment of FIG. 1A, the surfactant-modified composition is applied to the cation exchange media in a vessel until a predetermined pH change is detected in the effluent from the vessel, which indicates that the cation exchange media has reached its cation absorption capacity.

In some embodiments, multiple vessels may be used for the process.

FIG. 1B depicts a two-vessel embodiment of a system for use in the present invention. As shown in FIG. 1B, like the system of FIG. 1A, a raw feed, containing a composition containing onium ions and a process residue is provided. To this raw feed, a surfactant is added and the combined raw feed with the surfactant is pumped by a pump P into the first vessel. As shown in FIG. 1B, each vessel is provided with and contains a bed of cation exchange media, and initially, it has an initial bed height, shown as "1× Initial Bed Height". The pressure of the feed to each vessel is monitored by a pressure indicator PI. As the combined raw feed with the surfactant is pumped into the first vessel, the onium ions are absorbed by the cation exchange media, and the surfactant and any photoresist or other residue in the feed remains soluble or dispersed and passes through the first vessel. In this embodiment, the effluent from the first vessel is passed into the second vessel, where the onium ions are absorbed by the cation exchange media in the second vessel. As the combined raw feed with the surfactant is pumped into the second vessel, the onium ions are absorbed by the cation exchange media, and the surfactant and any photoresist or other residue in the feed remains soluble or dispersed and passes through the second vessel, and is collected and sent for disposal as appropriate. Thus, during the collecting step, the surfactant-modified composition is applied to the cation exchange media during which the onium ions become bound to and retained by the cation exchange media and the process residue and the surfactant do not become bound to the cation exchange media and are substantially not retained by the cation exchange media, in accordance with the present invention.

Thus, in the embodiment of FIG. 1B, in the collecting step of the process in accordance with the invention, the surfactant-modified composition is applied to the cation exchange media in the first vessel or column of the two vessels, a first effluent from the first vessel is applied as the feed to the cation exchange media in the second vessel of the two vessels, in a continuous series, until a predetermined pH change is detected in the effluent from the second vessel, at which time the recovering step may be carried out on at least the first vessel.

FIG. 1C depicts a three-vessel embodiment of a system for use in the present invention. As shown in FIG. 1C, like the systems of FIGS. 1A and 1B, a raw feed, containing a composition containing onium ions and a process residue is provided. To this raw feed, a surfactant is added and the combined raw feed with the surfactant is pumped by a pump P into the first vessel. As shown in FIG. 1C, each vessel is provided with and contains a bed of cation exchange media, and initially, it has an initial bed height, shown as "1× Initial Bed Height". The pressure of the feed to each vessel is monitored by a pressure indicator PI. As the combined raw feed with the surfactant is pumped into the first vessel, the onium ions are absorbed by the cation exchange media, and the surfactant and any photoresist or other residue in the feed remains soluble or dispersed and passes through the first vessel. In this embodiment, the effluent from the first vessel is passed into the second vessel, where the onium ions are absorbed by the cation exchange media in the second vessel. In this embodiment, the effluent from the second vessel next is passed into the third vessel, where the onium ions are absorbed by the cation exchange media in the third vessel. As the combined raw feed with the surfactant is pumped into the third vessel, the onium ions are absorbed by the cation exchange media, and the surfactant and any photoresist or other residue in the feed remains soluble or dispersed and passes through the third vessel, and is collected and sent for disposal as appropriate. Thus, in the collecting step, the surfactant-modified composition is applied to the cation exchange media during which the onium ions become bound to and retained by the cation exchange media and the process residue and the surfactant do not become bound to the cation exchange media and are substantially not retained by the cation exchange media, in accordance with the present invention.

Thus, in the embodiment of FIG. 1C, in the collecting step of the process in accordance with the invention, the surfactant-modified composition is applied as the feed to the cation exchange media in the first vessel or column of the three vessels, a first effluent from the first vessel is applied as the feed to the cation exchange media in a second vessel of the three vessels, and a second effluent from the second vessel is applied as the feed to the cation exchange media in the third vessel of the three vessels, in a continuous series, until a predetermined pH change is detected in the third effluent from the third vessel, at which time the recovering step may be carried out on the first or first and second vessels.

As is evident from the foregoing disclosure relating to FIGS. 1B and 1C, the at least two columns may be connected in a continuous series. Such series connections provides the ability to "switch out" vessels or columns that have reached their capacity of onium ion retention or, as undesirably sometimes occurs, have become blocked by excess process residue that has not been properly solubilized in accordance with the principles of the present invention. That is, if the amount of surfactant was inadequate to solubilize all of the process residue, and the column becomes partially blocked and channeling has resulted, that vessel or column can be removed from the series and cleaned and/or regenerated as need be to correct the problem.

As used herein, the term "solubilize" includes, but is not limited to, actual dissolution of a process residue but also includes any suspension, dispersion, etc., that results in the process residue substantially completely passing through the vessel or column and not blocking the cation exchange medium.

The surfactant in the present invention works similarly to any surfactant in aqueous solution, in that it solubilizes a material that would not otherwise be soluble at a given pH. In the present case, the process residue is soluble or substantially soluble at high pH, but when the pH becomes lower due to removal of the onium ions, the process residue would become insoluble and precipitate but for the added surfactant.

In one embodiment, the process is continued until a predetermined pH change is detected in the effluent from the vessel or column. In one embodiment, the predetermined pH change is detected either in the effluent from the first vessel. In one embodiment, the predetermined pH change is detected in the effluent from the second vessel. In one embodiment, the pH change is detected in the third effluent from the third vessel. In one embodiment, during the collecting step, the effluent from the vessel or column has a pH in the range from about pH 3 to about pH 4.5, or from about pH 3 to about pH 4, or about pH 3.5, prior to the time the respective vessel or column reaches its onium ion-holding capacity. Of course, if the vessel has become partially blocked and channeling has resulted, the vessel's onium-ion capacity will have been reduced. When either capacity has been reached, the observed pH of the effluent begins to rise, due to the release from the column of non-absorbed onium ions.

In one embodiment, in the collecting step, when the pH of the effluent from the vessel reaches pH 6, it is considered that the column has reached its capacity. In this embodiment, if the column bed height ratio has reached at least about 2.3, preferably at least about 2.5, the collection is considered to be complete. In this embodiment, if the column bed height ratio is less than about 2.3, this indicates that some portion of the cation exchange medium has been blocked by precipitated process residue, and the collection is considered to be incomplete.

In one embodiment, the recovering is carried out following detection of the predetermined pH change. Thus, for example, once the vessel effluent has reached about pH 6, the feed to that vessel is stopped, and usually is switched to another vessel. Then, the feed to the disconnected vessel is changed first to a rinse solution, and then to a high pH strong base solution, such as a solution of NaOH, KOH or LiOH. The rinse solution may contain deionized water and may also contain some amount of surfactant. The high pH strong base solution replaces the onium ions with the respective alkali metal ion used, i.e., $Na^+$, $K^+$ or $Li^+$, and the onium ions are freed from attachment to the anions of the cation exchange medium. As the removed onium ions flow from the vessel, they are recovered for eventual re-use.

In one embodiment, following the detection of the predetermined pH change, the third effluent is fed to a fourth vessel. The third vessel then becomes, in essence, the first vessel of the next series of vessels. In one embodiment, the system of vessels may include five vessels, and as the first vessel reaches its capacity, the feed is switched to the second vessel, and the effluent of the original third vessel is switched to feed the fourth vessel. Then, when the second vessel reaches its capacity, the effluent from the fourth vessel is switched to feed the fifth vessel. Meanwhile the recovering step can be applied to the first vessel and then to the second vessel.

In one embodiment, the system may include additional sensors for detecting pressure, pH, temperature, bed height or other relevant parameters of the vessels, ion exchange media, compositions in the vessels, as may be needed to provide a desired level of control. For example, an additional pH meter may be included at the bottom of the first column shown in FIG. 1B, or at the bottom(s) of the first and/or second column shown in FIG. 1C. The additional pH meter(s) would enable monitoring of the effluent from each column, and, for example, would thus enable the first column to be taken offline when it has reached its capacity, while continuing to apply the composition to the second or subsequent columns, thus enabling the recovery and regeneration of the first column without interrupting the process.

Surfactants

The most suitable surfactants for use in the present invention are surfactants which do not interact significantly with the cation exchange media and which are stable across a broad range of pH, such as from pH 3 to pH 14. Selection of a suitable surfactant may be based on the type of process residue, and the optimum surfactant may be determined through simple trial and error methods, with adjustments in either the identity or the quantity of surfactant made as needed to obtain the desired performance. For example, the process residue in many cases contains a photoresist residue, resulting from the removal of photoresist polymers by the onium ions. As is well known, there are many different photoresists, and for each photoresist waste system, the optimal surfactant (including identity and molecular weight range) and the optimal amount of the surfactant can be determined based on experience with the particular system, including consideration of the ion exchange media, the identity of the photoresist, the concentration of the photoresist residue in the waste stream, and other similar considerations. In some cases, a mixture of different surfactants and/or a mixture of molecular weight ranges of a single surfactant may be optimum. For example, for a DNQ-Novolak photoresist, the Novolak portion would, in the absence of surfactant, precipitate at a higher pH than would the DNQ portion. Thus, it may be optimal to use a combination of surfactants (or molecular weights) that are suited to solubilizing these two different portions of the process residue.

Simple laboratory experiments may be conducted to determine the optimal surfactant identity(ies) and concentration(s), without undue experimentation. Such simple laboratory experiments include, for example, provision of a composition containing the onium ion and a process residue, addition of a selected amount of a candidate surfactant, and then reduction of the pH to determine whether the process residue precipitates. If it does precipitate, either a different concentration of surfactant or a different surfactant is tried next. If no precipitation occurs, the surfactant and concentration should be sufficient for use in the collecting in accordance with the present invention. It may also be advisable to reduce the surfactant concentration of the non-precipitating test, to determine whether an even lower concentration of surfactant would work.

In one embodiment of the present invention, the surfactant is hydroxyl-containing nonionic surfactant. Nonionic surfactants generally meet the criteria for use in processes in accordance with the present invention.

In one embodiment of the present invention, the surfactant may include a hydroxyalkylcellulose, wherein alkyl is methyl, ethyl, propyl or butyl. In one embodiment, the surfactant includes a hydroxyethylcellulose. In one embodiment, the hydroxyethylcellulose has a molecular weight in the range from about 10,000 to about 1,000,000, preferably from about 200,000 to about 750,000.

In one embodiment the HEC has a molecular weight in the range from about 10,000 to about 1,000,000, or from about 100,000 to about 500,000, preferably about 250,000. In some commercially available HEC, the HEC is referred to as 2-hydroxyethyl cellulose (2-HEC) and in some cases as hydroxyethylecellulose (HEC). 2-HEC is available from Sigma-Aldrich in nominal average molecular weights Mv 90,000 (75-150 cP, 5 wt. % in $H_2O$ (25° C., Brookfield, spindle #1)(30 rpm)(lit.)), 250,000 (80-125 mP·s (lit.)), 720,000 (4,500-6,500 cP, 2 wt. % in $H_2O$ (25° C., Brookfield, spindle #4)(60 rpm)(lit.) and 1,300,000 (3,400-5,000 cP, 1 wt. % in $H_2O$ (25° C., Brookfield, spindle #4)(30 rpm)(lit.)). HEC is also available from Sigma-Aldrich with a viscosity of ~145 mPa·s, 1% in H$_2$O (20° C.), a viscosity of ~30 mPa·s, 1% in H$_2$O (20° C.), and a viscosity of 80-125 cP, 2% in H$_2$O (20° C.), but with no indication of molecular weight. HEC is available from Wako Pure Chemical Ind., Ltd. at viscosity (20 g/l, 20° C.) of 100-300 mPa·s, but with no indication of molecular weight. The foregoing information on viscosity and molecular weight is that provided by the manufacturer. Additional sources of HEC include Ashland and Dow Chemical.

In one embodiment of the present invention, the hydroxyl-containing nonionic surfactant may include a poly(ethyleneglycol)(PEG) or poly(ethyleneoxide)(PEO) having a molecular weight in the range from about 20,000 to about 2,000,000, in one embodiment a molecular weight of about 20,000 and in another embodiment at a molecular weight of about 200,000. As known in the art, this polymer is sometimes referred to as PEG at molecular weights below about 20,000 and as PEO at molecular weights above 20,000. Thus, reference to PEG or to PEO generally refer to the same polymer, possibly at different molecular weights, as noted. PEG/PEO is commercially available from Dow Chemical, among many others.

In one embodiment of the present invention, the surfactant may include a poly(vinylalcohol) (PVA). In one embodiment, the PVA may have a molecular weight in the range from about 20,000 to about 2,000,000, in one embodiment a molecular weight of about 66,000 to about 80,000. As is known in the art, PVA is prepared by hydrolysis of the ester polyvinylacetate, and any given PVA may include some residual ester in the polymer chain, and may also contain some monomer in the polymer chain lacking a hydroxyl group. The properties of the PVA may vary somewhat depending on the content of residual ester and/or missing hydroxyl groups. PVA is commercially available from Ashland and DuPont.

In one embodiment, the surfactant may include guar gum. Although varying, guar gum may have a molecular weight in the range from about 180,000 to about 200,000. Guar gum is commercially available from AV Gums and Polypro International.

In one embodiment of the present invention, the quantity of the selected surfactant in the surfactant-modified composition is in the range from about 10 ppm to about 10,000 ppm based on the total quantity of the surfactant-modified composition. In one embodiment of the present invention, the quantity of the selected surfactant in the surfactant-modified composition is in the range from about 100 ppm to about 5,000 ppm based on the total quantity of the surfactant-modified composition. In one embodiment of the present invention, the quantity of the selected surfactant in the surfactant-modified composition is in the range from about 200 ppm to about 1000 ppm based on the total quantity of the surfactant-modified composition. The minimum concentration of surfactant required to maintain solubility of the process residue should be used.

In one embodiment, the concentration of surfactant is adjusted according to the optical density (OD) of the incoming waste material, with a higher concentration of surfactant being used with higher OD waste. A rough estimate of the quantity of surfactant may be estimated by considering the OD of the composition containing onium ions and a process residue, the type of surfactant, the type of process residue, the concentration of the onium ions in the composition, and whether the composition containing onium ions and a process residue has been concentrated prior to providing to the process of the present invention. The OD of the composition generally varies with the concentration of any given process residue, but may not correlate across different process residues from different sources. OD reflects the amount of polymer in the composition, but may change with the source of the composition. Thus, for a given source of photoresist processing, there may be a reasonably consistent relationship between OD and polymer concentration, but the relationship may vary between sources. The OD is measured at an appropriate wavelength with a UV/visible spectrophotometer. For example, an appropriate wavelength for a Novolak residue is 305 nm.

Examples

In the following examples, samples of recycled compositions containing onium ions and process residue comprising a photoresist are treated in a process in accordance with embodiments of the present invention. In the following examples, a three-column setup, such as shown in FIG. 1C, is used.

Collection is conducted with three columns in series, such as that shown in FIG. 1C. During collection, the following parameters are recorded every hour: bed height of 1st column, bed height of 2nd column, bed height of 3rd column, 1st column pressure, 2nd column pressure, 3rd column pressure, and pH of effluent. During the collection, the pH of the effluent remains at about pH 3, and this pH will increase at or near the end of the collection. Collection is stopped when the third column effluent pH reaches 6. The 1st and 2nd columns are then used in the subsequent recovery step. The assay and OD of the recovered crude onium-containing waste material are measured. In embodiments using a different number of vessels or columns, collection is stopped when the effluent of the final column increases to pH 6.

In some cases, a series of collections is conducted, and following recovery, the columns are regenerated. In the succeeding collection, the third column in the previous collection becomes the first column, followed by the or other regenerated columns. In an alternate embodiment, four or more columns may be used, which can ensure that the process can be carried out continuously and without interruption.

The results of the collection tests are shown in Table 1. In the Table 1 results, the surfactants are hydroxyethylcellulose (HEC) and polyethyleneglycol (PEG). The "Assay (ppm)" shows the concentration of the surfactant added to the incoming waste material. Under the Collection Condition heading there is shown information on the incoming waste material, concentration of the onium ion as (Waste Assay) and the optical density ("Waste OD"). Column conditions include Flow rate (mL/h), OD/Assay (wt %), quantity of Surfactant/ (OD/Assay) (ppm·wt %). Under the Collection Data heading, there is shown the column height (cm), the normalized height of the first column at endpoint, the normalized height of the second column at endpoint, the maximum first column pressure (kPa) and the collection endpoint (pH). The collection outcome shows whether the collection was complete or incomplete, and the crude quality indicates the concentration and OD of the recovered onium hydroxide.

The HEC used in the Examples is obtained from Wako Pure Chemical Industries, Ltd. A 1 wt % stock solution of HEC is prepared, and added to the incoming composition containing the onium ions and the process residue as needed. The mixture is diluted with water to the indicated OD and assay. Each column is loaded with 250 mL of Lewatit weak acid ion exchange media. The media is preconditioned by treatment with 1 wt % HCl followed by deionized water. Collection is conducted at 16.7 mL/min. OD is measured with a UV-spectrophotometer and the onium ion assay is measured by titration.

TABLE 1

| | Surfactant | | Collection condition | | | | [Surfactant]/ | |
|---|---|---|---|---|---|---|---|---|
| Feed lot number | Type | Assay (ppm) | Waste assay (wt %) | Waste OD | Flow rate (mL/min) | OD/Assay (wt %$^{-1}$) | (OD/Assay) (ppm · wt %) | Column height (cm) |
| 22313 | N/A | 0 | 1.0 | 10 | 16.7 | 10.0 | 0.0 | 1800 |
| 22313 | PEG 20 | 4000 | 1.0 | 10 | 16.7 | 10.0 | 400.0 | 1500 |
| 62413 | HEC | 500 | 1.0 | 10 | 16.7 | 10.0 | 50.0 | 1500 |
| 62413 | HEC | 250 | 1.0 | 10 | 16.7 | 10.0 | 25.0 | 1800 |
| 60413 | HEC | 125 | 1.0 | 10 | 16.7 | 10.0 | 12.5 | 1800 |
| 60413 | HEC | 500 | 1.0 | 16 | 16.7 | 16.0 | 31.3 | 1800 |
| 60413 | HEC | 250 | 1.0 | 16 | 16.7 | 16.0 | 15.6 | 1500 |
| 52713 | HEC | 800 | 1.0 | 16 | 16.7 | 16.0 | 50.0 | 1800 |
| 52713 | HEC | 810 | 1.3 | 21 | 16.7 | 16.2 | 50.1 | 1500 |
| 52713 | HEC | 810 | 1.3 | 21 | 16.7 | 16.2 | 50.1 | 1500 |
| 52713 | HEC | 810 | 1.3 | 21 | 16.7 | 16.2 | 50.1 | 1500 |
| 82813 | N/A | 0 | 1.3 | 15 | 16.7 | 11.5 | 0.0 | 1800 |
| 82813 | HEC | 1000 | 1.3 | 15 | 16.7 | 11.5 | 86.7 | 1800 |
| 82813 | HEC | 1000 | 1.3 | 15 | 16.7 | 11.5 | 86.7 | 1800 |
| 82813 | HEC | 1000 | 1.3 | 15 | 16.7 | 11.5 | 86.7 | 1800 |
| 82813 | HEC | 1000 | 1.3 | 15 | 16.7 | 11.5 | 86.7 | 1800 |
| 82813 | HEC | 800 | 1.3 | 15 | 16.7 | 11.5 | 69.3 | 1800 |
| 82813 | HEC | 500 | 1.3 | 15 | 16.7 | 11.5 | 43.3 | 1800 |
| 82813 | HEC | 500 | 1.3 | 15 | 16.7 | 11.5 | 43.3 | 1800 |
| 82813 | HEC | 500 | 1.3 | 15 | 16.7 | 11.5 | 43.3 | 1800 |

| | Collection data | | | | | Crude quality | |
|---|---|---|---|---|---|---|---|
| Feed lot number | Normalized height of 1st column at endpoint | Normalized height of 2nd column at endpoint | Max 1st column pressure (kPa) | Collection endpoint (pH) | Collection outcome | TMAH assay | OD |
| 22313 | 2.19 | 1.27 | 107.9 | 6 | Incomplete | N/A | N/A |
| 22313 | 2.64 | 2.66 | 9 | 6 | Complete | 20.5 | 0.568 |
| 62413 | 2.65 | 2.73 | 8 | 6 | Complete | 20.5 | 0.237 |
| 62413 | 2.64 | 2.62 | 16 | 6 | Complete | 20.7 | 0.232 |
| 60413 | 2.23 | 1.76 | 256 | <6 | Incomplete | N/A | N/A |
| 60413 | 2.62 | 2.38 | 31 | 6 | Complete | 20.8 | 4.8 |
| 60413 | 1.67 | 1.16 | 92 | <6 | Incomplete | N/A | N/A |
| 52713 | 2.63 | 2.62 | 17 | 6 | Complete | 20.2 | 0.358 |
| 52713 | 2.63 | 2.53 | 11 | 6 | Complete | 20.8 | 0.607 |
| 52713 | 2.60 | 2.35 | 52 | 6 | Complete | 20.7 | 1.6 |
| 52713 | 2.39 | 2.37 | 31 | 6 | Complete | 20.1 | 1.5 |
| 82813 | 1.88 | 1.21 | 119 | 6 | Incomplete | N/A | N/A |
| 82813 | 2.60 | 2.46 | 18 | 6 | Complete | 20.7 | 0.898 |
| 82813 | 2.64 | 2.38 | 18 | 6 | Complete | 19.4 | 0.855 |
| 82813 | 2.38 | 2.34 | 27 | 6 | Complete | 20.1 | 1.81 |
| 82813 | 2.40 | 2.39 | 19 | 6 | Complete | 20.4 | 1.76 |
| 82813 | 2.61 | 2.54 | 17 | 6 | Complete | 20.7 | 0.472 |
| 82813 | 2.61 | 2.57 | 20 | 6 | Complete | 20.7 | 0.368 |
| 82813 | 2.63 | 2.33 | 71 | 6 | Complete | 19.3 | 1.53 |
| 82813 | 2.36 | 2.39 | 100.3 | 6 | Complete | 19.4 | 1.35 |

In the Examples and in Table 1, the bed height is an indication of the loading level of the cation exchange media. Normalized bed height is calculated by dividing the final bed height by the initial bed height, and is the ratio of the final bed height to the initial bed height. Normalized bed heights should be at least 2.3 for the cation exchange media used in the Examples. Where a collection is indicated as incomplete, one or both of pH endpoint of pH 6 and ratio of final to initial bed height less than 2.3 is observed. Collection may be discontinued if the column pressure becomes too great, since this indicates that precipitation has occurred within the column and the system is not working correctly. Typically, 100 kPa is the upper limit for laboratory processes, but may be higher in industrial processes, depending on the particular equipment.

Figure 2:
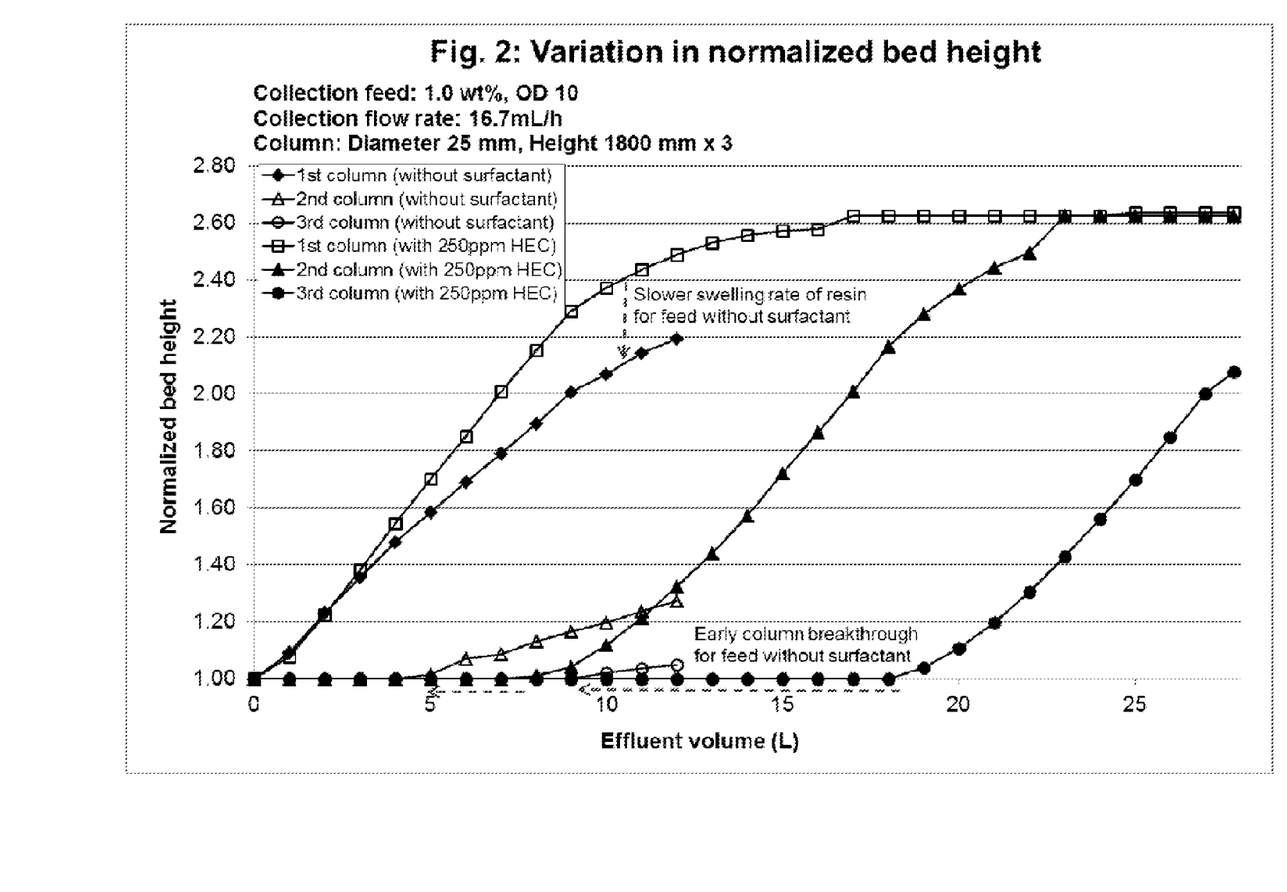
FIG. 2 is a graph depicting variation in normalized bed height for columns with and without surfactant, in accordance with certain embodiments of the invention and comparative examples.

FIG. 2 is a graph depicting variation in normalized bed height for columns with and without surfactant, in accordance with certain embodiments of the invention and comparative examples, in a three-column system such as that shown in FIG. 1C. As shown in FIG. 2, the normalized bed heights, i.e., the ratio of final to initial bed heights, is considerably higher for feeds applied with 250 ppm of HEC compared to the same feeds without surfactant. As is known in the art, as the cation exchange media absorbs the onium ions, it swells. A correlation can be established between initial/final bed height ratio and the loading of the onium ions in the cation exchange media. If the process residue precipitates and creates flow channels, thereby blocking some of the cation exchange media from contact with the composition containing the onium ions, the bed height will not increase sufficiently, and this can be a measure of whether sufficient surfactant is present in the composition. Thus, for feeds without surfactant, there may be one or more of slower overall swelling rates of the beds of cation exchange media, a lower ratio of bed heights, and an earlier breakthrough for feeds without surfactant.

Figure 3:
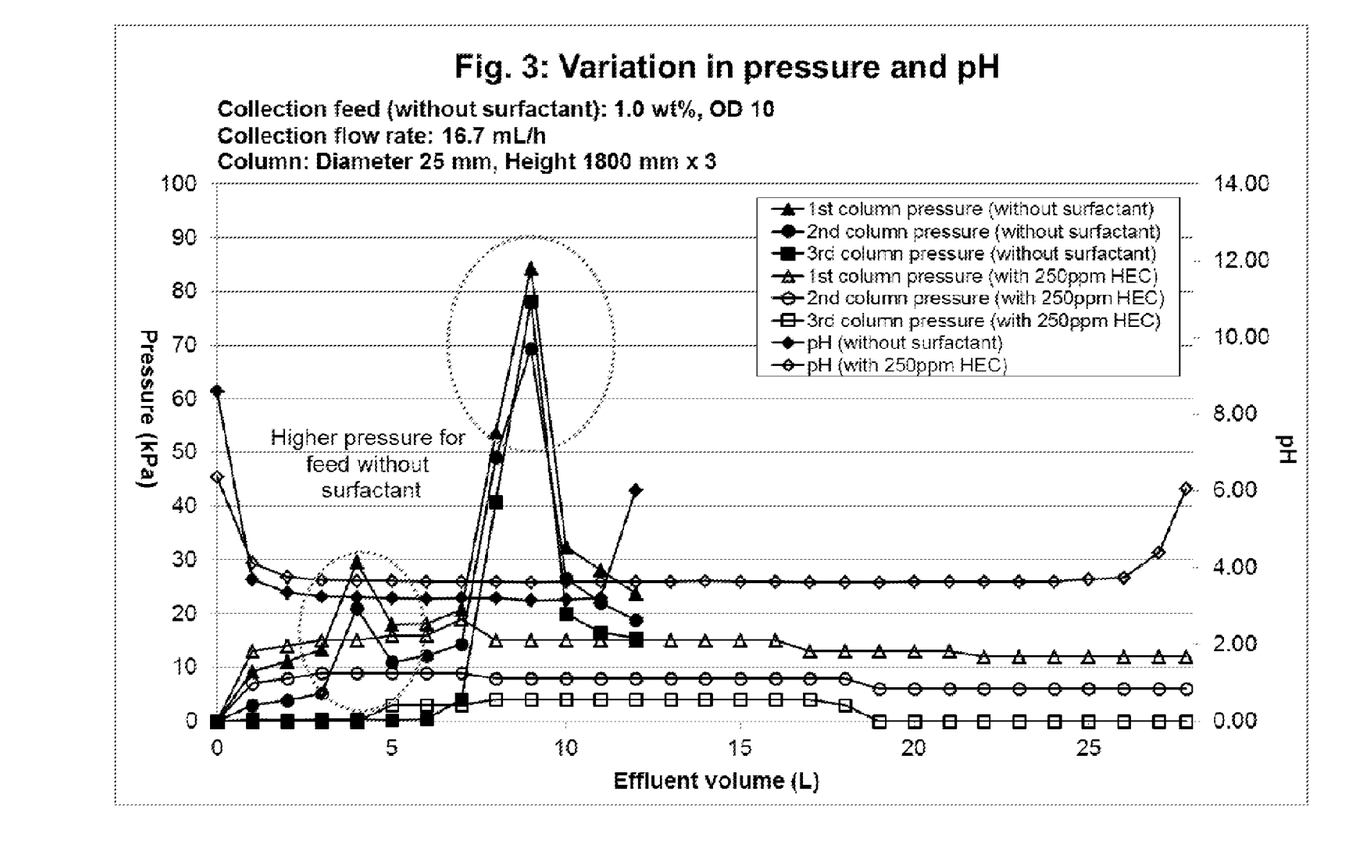
FIG. 3 is a graph depicting variation in pressure and pH for columns with and without surfactant, in accordance with certain embodiments of the invention and comparative examples.

FIG. 3 is a graph depicting variation in pressure and pH for columns with and without surfactant, in accordance with certain embodiments of the invention and comparative examples, in a three-column system such as that shown in FIG. 1C. As shown in FIG. 3, the column pressures in all three columns rapidly increase in the absence of added surfactant in the feed, whereas the column pressures remain steady or even decrease slightly in the feeds with surfactant, in accordance with the invention. As shown in FIG. 3, the pH of the effluent from the third column for the feeds without surfactant rapidly increases early in the collection, while the pH of the effluent from the third column only increases at a much later point in the collection for the feeds with surfactant, in accordance with the invention.

In the Examples and in the results shown in Table 1 and FIGS. 2 and 3, feeds without surfactant and in "incomplete" collections are comparative examples, while feeds with surfactant and "complete" collections are examples in accordance with the present invention.

It is noted that, throughout the specification and claims, the numerical limits of the disclosed ranges and ratios may be combined, and are deemed to include all intervening values. Furthermore, all numerical values are deemed to be preceded by the modifier "about", whether or not this term is specifically stated.

While the principles of the invention have been explained in relation to certain particular embodiments, which embodiments are provided for purposes of illustration, it is to be understood that various modifications thereof will become apparent to those skilled in the art upon reading the specification. Therefore, it is to be understood that the invention disclosed herein is intended to cover such modifications as fall within the scope of the appended claims. The scope of the invention is limited only by the scope of the appended claims.

The invention claimed is:

1. A process for recovering an onium hydroxide from a composition containing onium ions and a process residue, comprising:
providing a composition containing onium ions and a process residue;
adding a quantity of a surfactant to the composition to obtain a surfactant-modified composition;
providing a cation exchange media;
collecting the onium ions by applying the surfactant-modified composition to the cation exchange media wherein the onium ions become bound to and retained by the cation exchange media and the process residue and the surfactant do not become bound to the cation exchange media and are substantially not retained by the cation exchange media; and
recovering the onium ions from the cation exchange media as an onium hydroxide by applying a cation-containing hydroxide composition to the cation exchange media.

2. The process of claim 1 further comprising loading the cation exchange media into at least one vessel.

3. The process of claim 1 further comprising loading the cation exchange media into at least two vessels connected in series, wherein a first effluent from a first vessel of the at least two vessels may be applied as feed to a second vessel of the at least two vessels.

4. The process of claim 3 wherein in the collecting, the surfactant-modified composition is applied to the cation exchange media in the first vessel, the first effluent is applied as the feed to the second vessel, and the recovering is carried out on at least the first vessel when a predetermined pH change is detected in a second effluent from the second vessel.

5. The process of claim 3 wherein in the collecting, the surfactant-modified composition is applied to the cation exchange media in the first vessel, the first effluent is applied as feed to the cation exchange media in the second vessel, and a second effluent from the second vessel is applied as feed to the cation exchange media in a third vessel of the at least two vessels and a third effluent is obtained.

6. The process of claim 5, wherein the collecting is continued until a predetermined pH change is detected in the third effluent.

7. The process of claim 6 wherein the recovering is carried out on at least the first vessel following detection of the predetermined pH change.

8. The process of claim 6 wherein following the detection of the predetermined pH change, the third effluent is fed to a fourth vessel.

9. The process of claim 1 wherein the process residue comprises a photoresist residue.

10. The process of claim 1 wherein the onium is a quaternary ammonium.

11. The process of claim 10 wherein the quaternary ammonium has a general formula (I):

wherein in formula (I), $R^1$, $R^2$, $R^3$ and $R^4$ are each independently an alkyl group containing from 1 to about 8 carbon atoms.

12. The process of claim 1 wherein the surfactant is a hydroxyl-containing nonionic surfactant.

13. The process of claim 1 wherein the surfactant is a hydroxyalkylcellulose, wherein the alkyl is methyl, ethyl, propyl or butyl.

14. The process of claim 13 wherein the surfactant is a hydroxyethylcellulose.

15. The process of claim 14 wherein the hydroxyethylcellulose has a molecular weight in the range from about 10,000 to about 1,000,000, or from about 100,000 to about 500,000, or about 250,000.

16. The process of claim 12 wherein the hydroxyl-containing nonionic surfactant is a poly(ethyleneglycol) or poly(ethyleneoxide) having a molecular weight in the range from about 20,000 to about 2,000,000, or about 200,000.

17. The process of claim 12 wherein the surfactant is a poly(vinylalcohol) (PVA) having a molecular weight in the range from about 20,000 to about 2,000,000, or about 66,000 to about 80,000.

18. The process of claim 12 wherein the surfactant is a guar gum.

19. The process of claim 1 wherein the quantity of the selected surfactant in the surfactant-modified composition is in the range from about 10 ppm to about 10,000 ppm based on the total quantity of the surfactant-modified composition.

20. The process of claim 1 wherein the cation-containing hydroxide is sodium hydroxide, potassium hydroxide, lithium hydroxide, or a combination of any two or more thereof.

21. The process of claim 1 further comprising regenerating the cation exchange media by applying an acid to the cation exchange media.

* * * * *